United States Patent
Bhojaraja et al.

(10) Patent No.: US 11,869,657 B2
(45) Date of Patent: Jan. 9, 2024

(54) SYSTEMS AND METHODS FOR MANAGING FUTURE RADIOLOGY ORDERS

(71) Applicant: CERNER INNOVATION, INC., Kansas City, KS (US)

(72) Inventors: Kiran Bhojaraja, Bengaluru (IN); Vikram Nandwani, Bengaluru (IN); Hemalatha Raghaviah, Bangalore (IN); Deepak Gupta, Bangalore (IN); Bobbie Milne, Kansas City, MO (US); Tania Bharracharyya, Bengaluru (IN); Premjit Adhikary, Bongaigaon (IN); Roopa Krishnappa, Bangalore (IN); C. G. Bhuvaneshwari, Bangalore (IN)

(73) Assignee: CERNER INNOVATION, INC., Kansas City, MO (US)

( * ) Notice: Subject to any disclaimer, the term of this patent is extended or adjusted under 35 U.S.C. 154(b) by 186 days.

(21) Appl. No.: 17/135,154

(22) Filed: Dec. 28, 2020

(65) Prior Publication Data
US 2021/0202080 A1 Jul. 1, 2021

(51) Int. Cl.
*G16H 40/20* (2018.01)
*G16H 10/60* (2018.01)
*G16H 40/63* (2018.01)
*G16H 40/40* (2018.01)

(52) U.S. Cl.
CPC ............ *G16H 40/20* (2018.01); *G16H 10/60* (2018.01); *G16H 40/40* (2018.01); *G16H 40/63* (2018.01)

(58) Field of Classification Search
CPC ........ G16H 40/20; G16H 10/60; G16H 40/40; G16H 40/63
USPC .......................................................... 705/2–3
See application file for complete search history.

(56) References Cited

U.S. PATENT DOCUMENTS

| | | | | |
|---|---|---|---|---|
| 7,634,419 B1* | 12/2009 | Travis | ................... | G16H 10/60 726/28 |
| 7,729,928 B2* | 6/2010 | Backhaus | .............. | G16H 30/40 705/2 |
| 11,450,416 B2* | 9/2022 | Pillarisetty | ............. | G16H 40/67 |
| 2006/0195339 A1* | 8/2006 | Backhaus | .............. | G16H 10/60 705/2 |
| 2006/0212317 A1* | 9/2006 | Hahn | ..................... | G16H 40/20 382/128 |
| 2007/0078679 A1* | 4/2007 | Rose | ....................... | G16H 15/00 600/300 |
| 2008/0292152 A1* | 11/2008 | Nekrich | ................. | G16H 30/40 382/128 |
| 2009/0198520 A1* | 8/2009 | Piovanetti-Perez | ......... | G06Q 10/087 705/26.1 |
| 2011/0004490 A1* | 1/2011 | Backhaus | .............. | G16H 30/40 705/2 |
| 2011/0066449 A1* | 3/2011 | Backhaus | .............. | G06Q 99/00 705/2 |

(Continued)

*Primary Examiner* — Michael Tomaszewski
(74) *Attorney, Agent, or Firm* — KRAGULJAC LAW GROUP, LLC (57) ABSTRACT

Computerized systems and methods are provided for managing future radiology orders for multiple facilities. The systems and methods can include detecting a location identifier for each future radiology order, and in response to detecting the location identifier, determining a specific radiology facility for that location identifier. The respective future radiology orders can then be provided to the intended radiology facility.

20 Claims, 8 Drawing Sheets

(56) References Cited

U.S. PATENT DOCUMENTS

| | | | | |
|---|---|---|---|---|
| 2015/0150092 A1* | 5/2015 | Raizada | ............... | H04L 63/08 726/4 |
| 2015/0294071 A1* | 10/2015 | Machtelinck | ......... | G06Q 10/06 705/2 |
| 2015/0347693 A1* | 12/2015 | Lam | ................ | G16H 40/20 705/3 |

* cited by examiner

☐ Prompt

510  Field description:
First Location Identifier Field

Catalog type:
Radiology

Event Code

Field type:
Type A

Validation type:
Type 1

Meaning:
User defined field

Code Set A:
140125  ← 520

Accept size: Help context: Spin increment:
32            4              9

Minimum value:
0

Maximum value:
0

☐ Hide from common order details window
☐ Allow multiple occurrences of field
☐ Make field as wide as the window
☐ Enable interface mapping OK   Close

| | Value | Value Display | Location | |
|---|---|---|---|---|
| | | | | |

Code Set A ...

| | Value | Value Display | Location | |
|---|---|---|---|---|
| 1 | 31867842 | Loc 1 | 1648352.00 | ⊖ |
| 2 | 31867846 | Loc 2 | 1648417.00 | ⊖ |
| 3 | 31867850 | Loc 3 | 1648571.00 | ⊖ |

SYSTEMS AND METHODS FOR MANAGING FUTURE RADIOLOGY ORDERS

CROSS-REFERENCE TO RELATED APPLICATIONS

This application claims priority to Indian Application No. 201941054673, filed Dec. 31, 2019, the entire contents of which are incorporated by reference herein.

BACKGROUND

In certain conventional systems, future orders for radiology services are provided to a default facility, which may not be the facility where the order originated or where the radiology procedure is intended to be performed. In such systems, a radiologist and/or a radiology facility may not be aware of these orders until it has been scheduled, leaving a short timeframe for the radiologist to vet and/or protocol these orders. Therefore, there is a need to develop new systems and processes for managing future radiology orders.

BRIEF DESCRIPTION OF THE SEVERAL VIEWS OF THE DRAWINGS

The present invention is described in detail below with reference to the attached drawing figures, wherein.

DETAILED DESCRIPTION

The description of various systems and processes herein is provided to meet statutory requirements. However, the description itself is not intended to limit the scope of the claims. Rather, it is contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Aspects of the present disclosure relate to systems and methods for managing future radiology orders. In aspects, the systems and methods for managing future radiology orders can include managing radiology orders for a plurality of radiology facilities. Prior to the use of electronic medical records, in certain conventional systems, when a medical professional ordered a radiology procedure for an individual, the individual may directly communicate with the radiology facility to schedule the procedure, and at that time the radiologist may then vet and/or protocol the order. However, with the use of electronic medical records, in conventional systems as discussed above, the future radiology orders would be sent to a default facility that may not be the facility where the order originated or where the radiology procedure is intended to be performed. In such conventional systems, sending large volumes of future radiology orders to a default facility is additionally problematic within electronic medical records for a large, multi-facility organization. For instance, in such conventional systems, the intended radiologist and/or intended radiology facility for specific future radiology orders may not be aware of the future radiology orders that are specific to that radiologist and/or radiology facility. While in such conventional systems, the radiologist and/or radiology facility may be able to access all the future orders at the default facility/location, there would be no way for that radiologist and/or facility to know which future radiology orders they are to vet, schedule, and/or perform. Rather in these conventional systems, the radiologist and/or radiology facility would likely be required to wait until orders from the default location are scheduled for their facility prior to such orders being vetted.

Further, in conventional systems, due to future radiology orders not being directly sent to the facility and/or radiologist where the intended procedure is to be carried out, the radiologist may not have sufficient lead-time to vet and/or protocol such future orders. In such scenarios, since the radiologist (and/or radiology facility) is vetting already scheduled radiology orders, the vetting and scheduling process itself can be inefficient. For example, since the radiologist may be vetting already scheduled radiology orders, any changes or preliminary procedures that need to be performed may require a re-ordering of the scheduled individuals for a given day or week. Further, during the vetting process, a radiologist may desire to change a specific radiology order or procedure, which may also disrupt the current schedule of procedures for the radiologist and/or the radiology facility. Additionally, certain multi-facility medical organizations may generate a large volume of clinical orders, e.g., radiology orders, so the inefficiencies discussed above can accumulate into longer wait times and delayed procedures. Further, such inefficiencies also may unnecessarily reduce the amount of radiology orders or procedures that get completed in a day.

The systems and methods described herein can alleviate one or more of the problems described above. For instance, in certain aspects, the system and methods described herein can provide for the management of a plurality of future radiology orders by including in the future radiology orders a location identifier. Location identifiers in future radiology orders as described herein, which could be used to route the future radiology orders to the intended radiology facility and/or intended radiologist, are not provided in conventional systems. In aspects, the location identifier can be associated with a specific radiology facility where a specific radiology order is intended to be performed. As such, in certain aspects, the systems and methods described herein can include detecting a location identifier for each future radiology order, and in response to detecting the location identifier, determining a specific radiology facility for that location identifier, and providing the radiology order to the intended specific radiology facility. By routing the future radiology orders to the intended radiology facility, a radiologist and/or the specific radiology facility receives a specific subset of the large volume of the plurality of future radiology orders, with this subset of orders intended to be performed at that specific facility. This is distinct from the conventional systems, where future radiology orders were indiscriminately provided to a default location or facility, prior to ending up at an intended facility. As such, in aspects, the systems and methods described herein reduce overall processor use, and thereby free up processing power and memory for other operations, since the future radiology orders do not need to be sent first to a default facility prior to sending them to the intended facility.

Further, in aspects, the radiologist and/or radiology facility, using the systems and methods described herein, can review all or any portion of orders that are intended specifically for that radiologist or for a specific radiology facility. In such aspects, this specific subset of future radiology orders can be reviewed, updated, canceled, and/or ranked by the intended radiologist or facility, prior to scheduling the orders, which may maximize the efficiency of the electronic medical record system and or radiology order system, in addition to the efficiency of a facility's time and use of resources.

The ranking and vetting process of future radiology orders prior to scheduling the orders, in aspects, can be an important step in managing large volumes of future orders for multiple facilities, where increased efficiency can reduce long wait-times. Additionally, the systems and methods disclosed herein can reduce errors in managing large volumes of future orders, which in aspects may also increase efficiencies. For example, in conventional systems, large volumes of future radiology orders may be routed to a default facility that may be linked to the specific procedure. However, errors may arise in the further scheduling of these future orders using the conventional systems at such a default location, as this default location that received the future orders may not be the facility where the procedure is intended to be performed. At least in this way, such conventional systems provide increased exposure to scheduling errors, among other errors. However, with the systems and methods described herein, a location identifier is included with the future radiology order allowing such orders to be automatically routed to the intended radiology facility and/or intended radiologist as opposed to a default location used in conventional systems, thereby eliminating the potential errors encountered in the conventional systems described above.

Accordingly, in one aspect, a computerized system is provided. The computerized system can include one or more processors and non-transitory computer storage media storing computer-useable instructions. The computer-useable instructions, when used by the one or more processors, cause the one or more processors to receive a plurality of future radiology orders, where the plurality of future radiology orders includes radiology orders for a plurality of radiology facilities; and detect a location identifier associated with at least a portion of the plurality of future radiology orders. Additionally, the computer-useable instructions, when used by the one or more processors, cause the one or more processors to, based on detecting a location identifier associated with each of the at least a portion of the plurality of future radiology orders, determine a specific radiology facility intended for each of the at least a portion of the plurality of future radiology orders; and provide to each specific radiology facility, radiology orders of the at least a portion of the plurality of future radiology orders intended for each specific radiology facility.

In another aspect, a computerized system is provided. The computerized system can include one or more processors and non-transitory computer storage media storing computer-useable instructions. The computer-useable instructions, when used by the one or more processors, cause the one or more processors to receive a plurality of future radiology orders, where the plurality of future radiology orders includes radiology orders for a plurality of radiology facilities; and determine that at least a first portion of the plurality of future radiology orders includes a first location identifier, the first location identifier associated with a first radiology facility. Additionally, the computer-useable instructions, when used by the one or more processors, cause the one or more processors to provide the at least a first portion of the future of radiology orders to the first radiology facility.

In yet another aspect, a computerized system is provided. The computerized system can include one or more processors and non-transitory computer storage media storing computer-useable instructions. The computer-useable instructions, when used by the one or more processors, cause the one or more processors to receive a plurality of future radiology orders. The plurality of future radiology orders can include radiology orders for at least ten radiology facilities, and one or more of the plurality of future radiology orders can be provided from a facility that is different from the plurality of radiology facilities. The plurality of future radiology orders can also include orders for individuals not present at one of the plurality of radiology facilities at the time the respective orders were created. Additionally, the computer-useable instructions, when used by the one or more processors, cause the one or more processors to detect a location identifier associated with at least a portion of the plurality of future radiology orders, wherein the location identifier is provided at the time the order is provided. Further, the computer-useable instructions, when used by the one or more processors, cause the one or more processors to, based on detecting a location identifier associated with each of the at least a portion of the plurality of future radiology orders, determine a specific radiology facility intended for each of the at least a portion of the plurality of future radiology orders; and provide to each specific radiology facility, radiology orders of the at least a portion of the plurality of future radiology orders intended for each respective specific radiology facility.

As used herein, the term "future radiology order(s)" refers to a radiology order(s) that is for a radiology procedure, or for an examination by a radiologist, at a time after the future radiology order originated. For example in aspects, a future radiology order can be for a radiology procedure or radiologist examination that is at least one day or at least one week after the future radiology order originated. In aspects, a future radiology order can have originated at a facility that is distinct, or at a different location, from the intended radiology facility.

Figure 1:
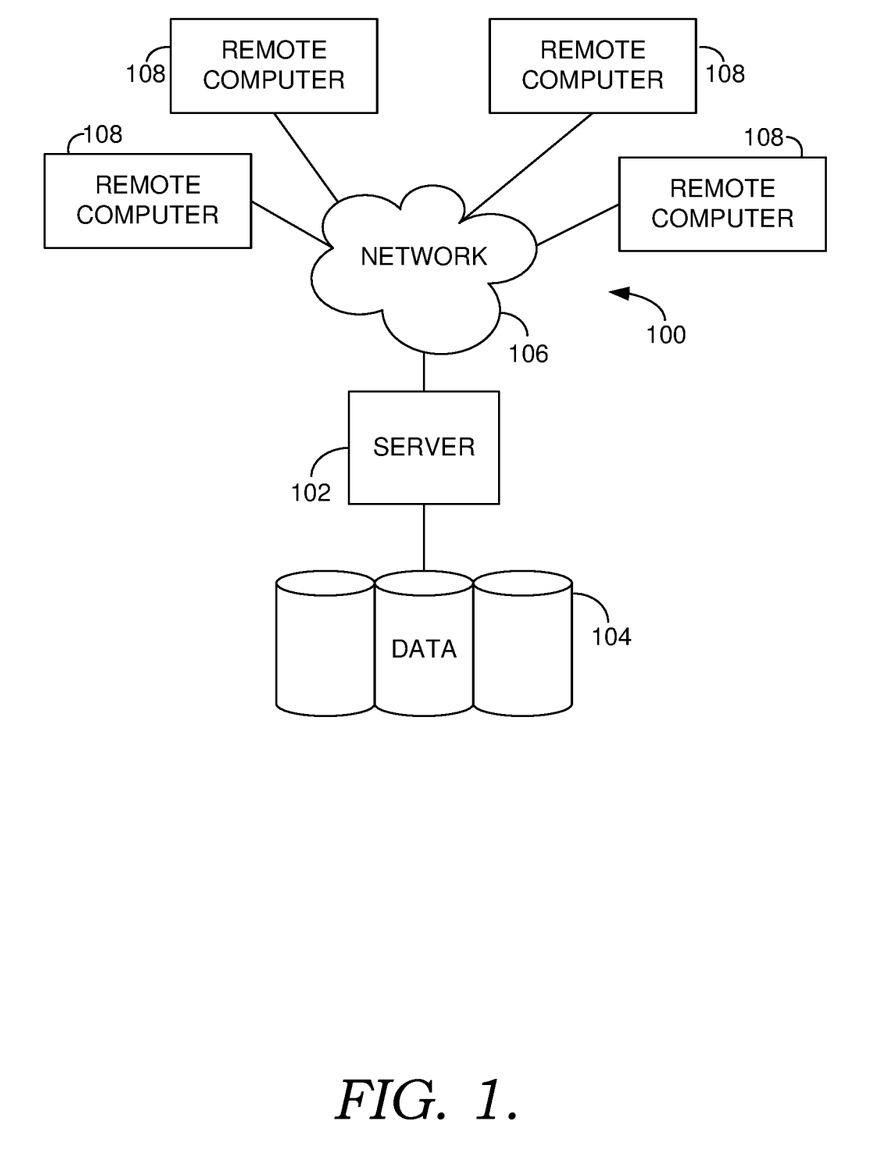
FIG. 1 is a block diagram of an exemplary system architecture in which embodiments of the invention may be employed, in accordance with aspects herein.

Turning now to the figures, and to FIG. 1 in particular, an example computing environment suitable for use in implementing embodiments of the present invention is shown. FIG. 1 is an example computing environment (e.g., health-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein. It will be appreciated by those having ordinary skill in the art that the connections illustrated in FIG. 1 are also exemplary as other methods, hardware, software, and devices for establishing a communications link between the components, devices, systems, and entities, as shown in FIG. 1, may be utilized in the implementation of the systems and methods disclosed herein. Although the connections are depicted using one or more solid lines, it will be understood by those having ordinary skill in the art that the exemplary connections of FIG. 1 may be hardwired or wireless, and may use intermediary components that have been omitted or not included in FIG. 1 for simplicity's sake. As such, the absence of components from FIG. 1 should not be interpreted as limiting the systems and methods disclosed herein to exclude additional components and combination(s) of components. Moreover, though devices and components are represented in FIG. 1 as singular devices and components, it will be appreciated that some embodiments may include a plurality of the devices and components such that FIG. 1 should not be considered as limiting the number of a device or component.

The present technology might be operational with numerous other special-purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The systems and methods disclosed herein may be operational and/or implemented across computing system environments such as a distributed or wireless "cloud" system. Cloud-based computing systems include a model of networked enterprise storage where data is stored in virtualized storage pools. The cloud-based networked enterprise storage may be public, private, or hosted by a third party, in embodiments. In some embodiments, computer programs or software (e.g., applications) are stored in the cloud and executed in the cloud. Generally, computing devices may access the cloud over a wireless network and any information stored in the cloud or computer programs run from the cloud. Accordingly, a cloud-based computing system may be distributed across multiple physical locations.

The present technology might be described in the context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Computer-readable media does not include signals per se.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations including operating systems, device drivers and the like. The remote computers might also be physically located in traditional and nontraditional clinical environments so that the entire medical community might be capable of integration on the network. The remote computers might be personal computers, servers, routers, network PCs, peer devices, other common network nodes, or the like and might comprise some or all of the elements described above in relation to the control server. The devices can be personal digital assistants or other like devices. Further, remote computers may be located in a variety of locations including in a medical or research environment, including clinical laboratories (e.g., molecular diagnostic laboratories), hospitals and other individual settings, veterinary environments, ambulatory settings, medical billing and financial offices, hospital administration settings, home medical environments, and clinicians' offices. Medical providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional clinical environments so that the entire medical community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote medical device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
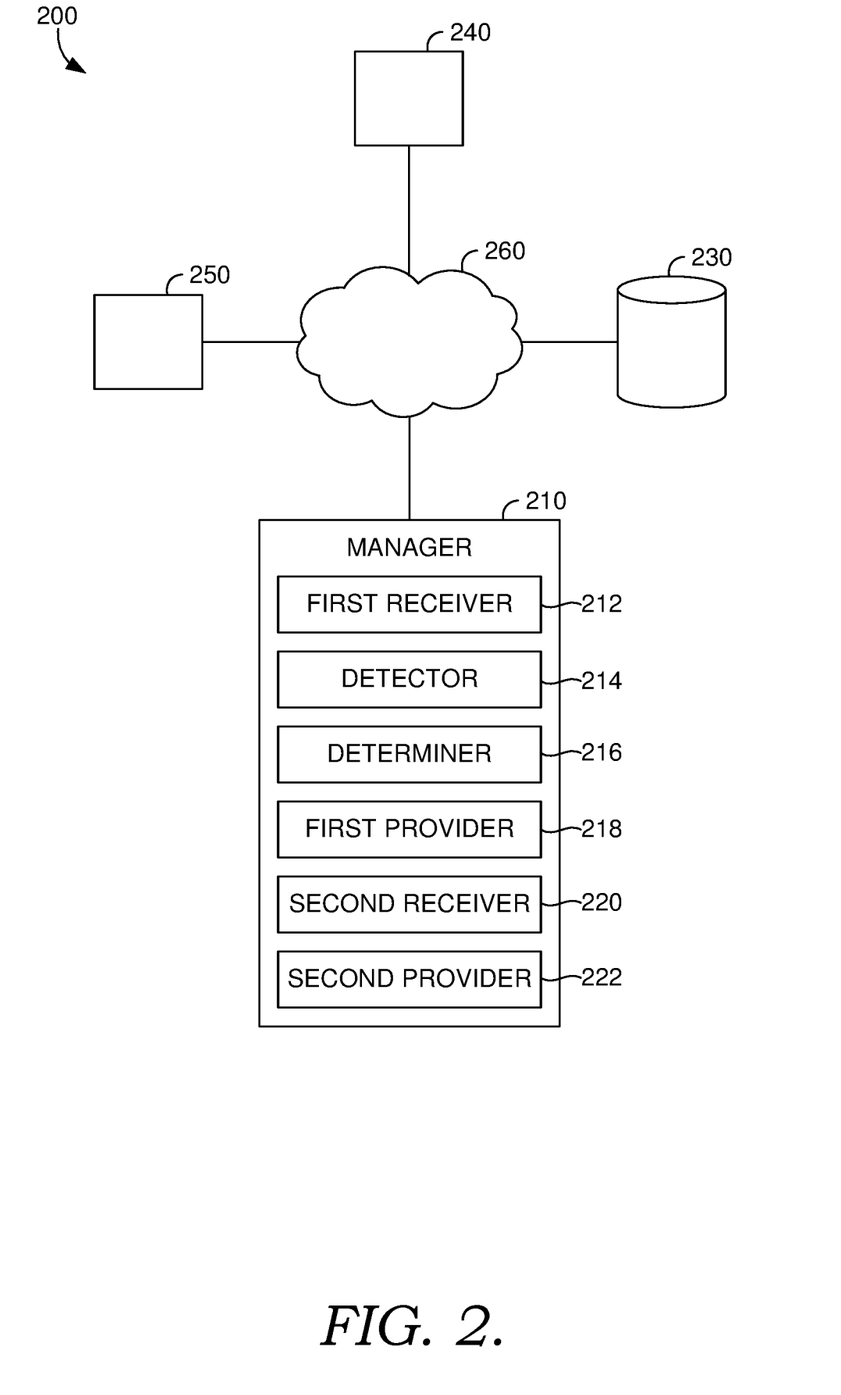
FIG. 2 is an exemplary system architecture for managing future radiology orders, in accordance with aspects herein.

Turning now to FIG. 2, an example system, system 200, for managing future radiology orders is depicted. The system 200 is merely an example of one suitable system and is not intended to suggest any limitation as to the scope of use or functionality of embodiments of the present disclosure. Neither should the system 200 be interpreted as having any dependency or requirement related to any single component or combination of components illustrated herein.

In certain aspects, the system 200 can include the features and properties of one or more of the components of the computing environment 100 of FIG. 1. In the same or alternative aspects, the system 200 can operate and/or function within the computing environment 100 of FIG. 1.

The exemplary system 200 comprises a manager 210, a database, 230, a network 260, a computer server 240, and an application 250. As shown, FIG. 2 includes one manager 210, one database, 230, one network 260, one computer server 240, and one application 250. However, it is contemplated that the system 200 may comprise more than one of each of these components depending on the needs of the system 200. For example, the system 200 may comprise more than one database 230, which may be located remotely or on the cloud.

In various aspects, the database 230 of FIG. 2 can include one or more future radiology orders. In certain aspects, each of the future radiology orders can be associated with one or more electronic medical records. In certain aspects, the database 230 can be a database comprised of electronic medical records and associated future radiology orders. In various aspects, the future radiology orders are electronic orders, and/or are orders created using a software application and/or electronic medical record management system.

As depicted, the system 200 comprises a manager 210. It will be appreciated that some or all of the subcomponents of the manager 210 may be accessed via the network 260 and may reside on one or more devices. Additionally, the manager 210 may also be integrated into the application 250. It is contemplated that the application 250, in aspects, may be an electronic health record system for multiple individuals of a multi-facility medical organization. Further, in some embodiments, one or more of the illustrated components of the manager 210 may be implemented as a stand-alone application. The components described are exemplary in nature and in number and should not be construed as limiting. Any number of components may be employed to achieve the desired functionality within the scope of the embodiments hereof.

In aspects, the manager 210 is configured to manage a plurality of future radiology orders. In certain aspects, at a high level, the manager 210 can, among other features, detect location identifiers in a plurality of future radiology orders, determine the specific radiology facility and/or specific radiologist associated with that location identifier, and provide to the specific radiology facility and/or specific radiologist future radiology orders having that specific location identifier.

As can be seen in the aspect depicted in FIG. 2, the manager 210 can include a first receiver 212, a detector 214, a determiner 216, a first provider 218, a second receiver 220, and a second provider 222.

In aspects, the first receiver 212 can receive, via the network 260, one or more future radiology orders, e.g., future radiology orders that may be stored in the database 230. In certain aspects, the receiver 212 may be configured to automatically query the database 230 for any new future radiology orders and receive the same, or may automatically receive new future radiology orders without querying the database.

In certain aspects, the detector 214 can detect a location identifier that may be present with, or associated with, the future radiology orders. In certain aspects, as discussed further below with respect to FIGS. 3 and 4, detection of a location identifier can include determining if a location identifier was entered into a specific information field of the future radiology order.

In various aspects, based on a location identifier being detected in a received future radiology order, the determiner 216 can determine a specific radiology facility intended for the future radiology order. In certain aspects, as discussed further below, determining a specific radiology facility intended for the future radiology order can include reading the detected location identifier. In the same or alternative aspects, the determiner 216 can read the location identifier and use the location identifier to determine the radiology facility associated with that location identifier, e.g., via a lookup table or other convenient operation.

In aspects, once the specific radiology facility has been determined, the first provider 218 can provide to the specific radiology facility and/or to a specific radiologist the future radiology orders intended for that facility. In aspects, the first provider 218 can provide future radiology orders to a radiology facility and/or a radiologist in any convenient manner. In one aspect, the first provider 218 can send, e.g., via the network 260, the future radiology orders to the intended radiology facility and/or intended radiologist. In the same or alternative aspects, the first provider 218 can provide the future radiology orders to a device, server, or database associated with the intended radiology facility and/or intended radiologist, such as the computer server 240. In aspects, the device, server, or database associated with the intended radiology facility and/or intended radiologist may be different from the database 230. In various aspects, providing the future radiology orders to a intended radiologist or radiology facility can include providing access permission to the future radiology orders residing in the system 200, e.g., in the database 230.

In certain aspects, once the future radiology orders are provided to the intended radiology facility and/or to the intended radiologist, the radiology facility and/or the radiologist may vet the future orders. In such aspects, the radiologist may review the future radiology order, accept the order as it is, cancel the order, or replace it with a new order. In one aspect, the radiologist may review the order so that the radiologist and the facility are aware of the specific intended procedure, and can then know what instrumentation, contrast agents, multi-phase studies, and the like, are required, if any, for such a procedure. In such aspects, this information may aid in arranging the schedule of procedures for the radiologist and/or radiology facility.

In various aspects, where a radiologist and/or radiology facility creates a replacement order, the first receiver 212 can receive the replacement order, e.g., for storage in the database 230 and/or to update an electronic medical record. Optionally, the manager 210 can provide, e.g., via the network 260, the replacement order to the originating medical professional that created the future radiology order for their records and/or their approval.

In various aspects, a radiologist and/or radiology facility may request certain future radiology orders from the database 230. In one aspect, the radiologist and/or radiology facility may request certain future radiology orders by querying the system 200 using a location identifier. In such aspects, the second receiver 220 of the manager 210 can receive a request, e.g., from the radiologist and/or radiology facility, for certain radiology orders. Further, in such aspects, the manager 210 can receive future radiology orders, detect the queried or requested location identifier, and provide the requested future radiology orders to the radiologist or radiology facility, via the second provider 222 of the manager 210.

Figure 3:
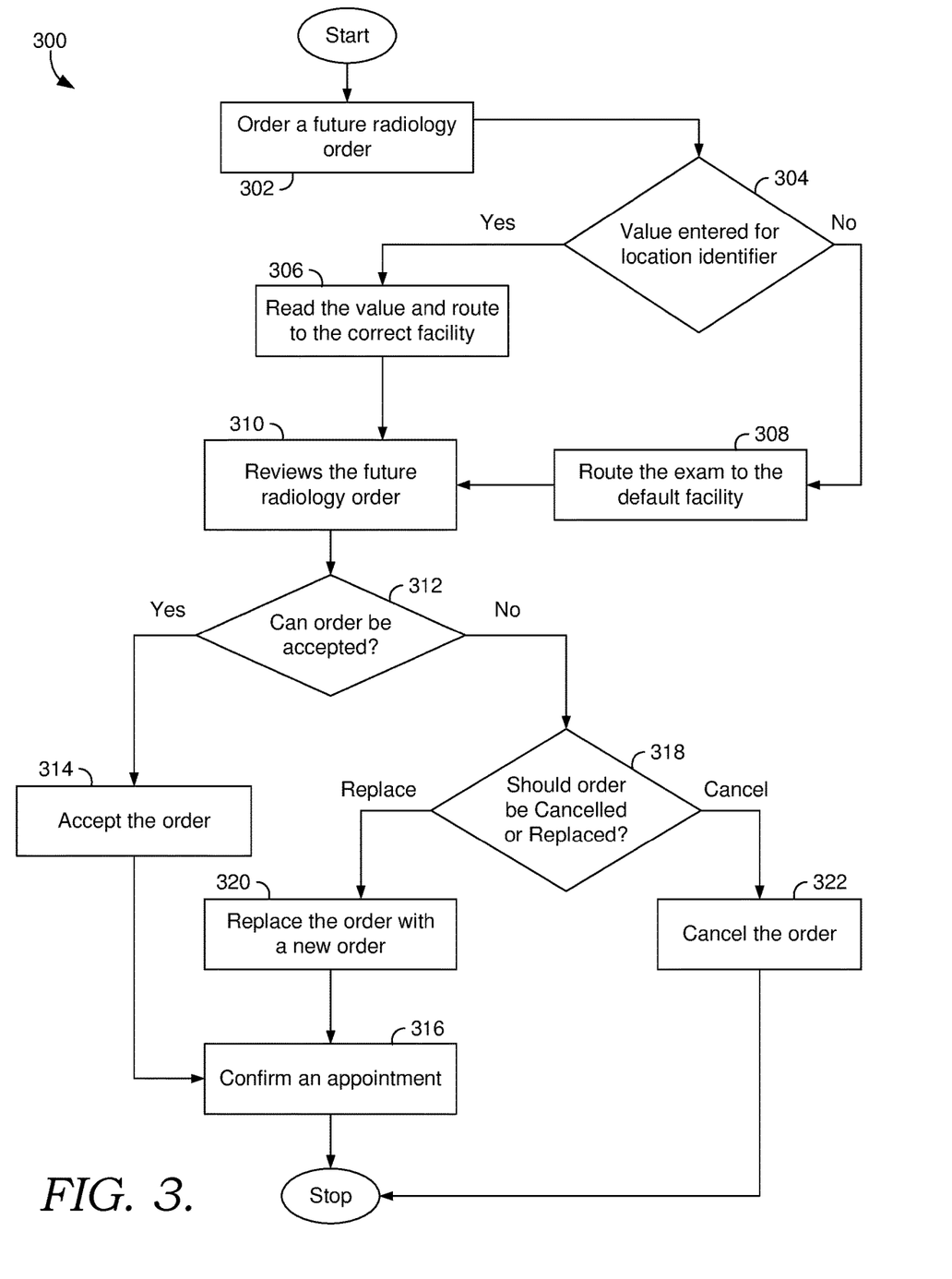
FIG. 3 is a flow diagram of an example method for managing future radiology orders, in accordance with aspects herein.

FIG. 3 depicts a flow chart for one example method 300 for use in the certain aspects of the systems described herein. In various aspects, the system 200 of FIG. 2 described above can be utilized to carry out all or a part of the method 300. The method includes the step 302 where a future radiology order originates or is ordered. In aspects, the future radiology order can be prepared by an originating medical professional that is at a different facility and/or at a different physical location than that of the intended radiology facility or radiologist. In aspects, the originating medical professional may be associated with the same medical provider or organization as the radiologist and/or radiology facility. In alternative aspects, the originating medical professional may not be associated with the same medical provider or organization as the radiologist and/or radiology facility, and may intend for the future radiology order to be for a third-party radiologist and/or radiology facility. In the same or alternative aspects, one or more of the originating medical professional, the radiologist, or the radiology facility may be associated with a multi-facility medical provider or organization. In such aspects, the future radiology order may be provided from the originating medical professional to an electronic medical records application or system associated with a multi-facility medical provider or organization, which may, in aspects, be stored in a database, such as the database 230 of the system 200 of FIG. 2.

At step 304 of the method 300, it is determined whether a location identifier is provided or associated with the future radiology order. As discussed further below, location identifiers can be provided along with future radiology orders via a location identifier field associated with the future radiology order. In certain aspects, a medical provider or organization utilizing an electronic medical records system or application may specify different fields of a future radiology order application as the location identifier field, in order to allow for customization. Below, one example method for determine whether or not a location identifier is present in a location identifier field in discussed in detail with respect to FIG. 4. If at step 304, a location identifier is absent in the future radiology order, then the future radiology order is routed to a default facility, as may be done in the conventional systems discussed above. As discussed above, such a default facility may not be the intended radiology facility for performing the procedure specified in the radiology order. In aspects, even if the future radiology order is routed to a default facility, ultimately the future radiology order will be provided to the intended radiologist and/or radiology facility. However, as discussed above, this conventional routing includes the extra step of first sending the future radiology order to a default facility where the future radiology order is stored with other radiology orders with no discrete discernable location identifier. This conventional routing can make retrieval of a desired subset of future radiology orders for a specific facility difficult and/or delay the provision of a subset of orders to the intended facility.

If at step 304, a location identifier is detected, e.g., a location identifier is associated with the future radiology order, then at step 306 the specific radiology facility is determined based on the detected location identifier. As discussed above, determining a specific radiology facility intended for the future radiology order can include reading the detected location identifier and/or using that location identifier to determine the radiology facility associated with that location identifier.

At step 310, a radiologist and/or another at a radiology facility reviews the received future radiology orders. As discussed above, in aspects, the radiologist and/or radiology facility will review the ordered procedure to determine if it is an appropriate procedure and/or so that the radiologist and the facility are aware of any specific requirements for that procedure, e.g., instrumentation, contrast agents, multiphase studies, and the like. At step 312, it is determined if the future radiology order can be accepted, and if so, at step 314, the order is accepted. In aspects, at step 316 future orders accepted or confirmed by the radiology facility or the radiologist are scheduled and the appointment is confirmed.

If at step 312, the future order cannot be accepted by the radiologist and/or the radiology facility, at step 318 it is determined if the future radiology order is to be canceled or replaced. If the order is to be canceled, at step 322 the order is canceled. If at step 318 it is determined that the future radiology order should be replaced with a new order, at step 320 the order is replaced with a new radiology order, where at step 316 a scheduled appoint for the new order is confirmed.

Figure 4:
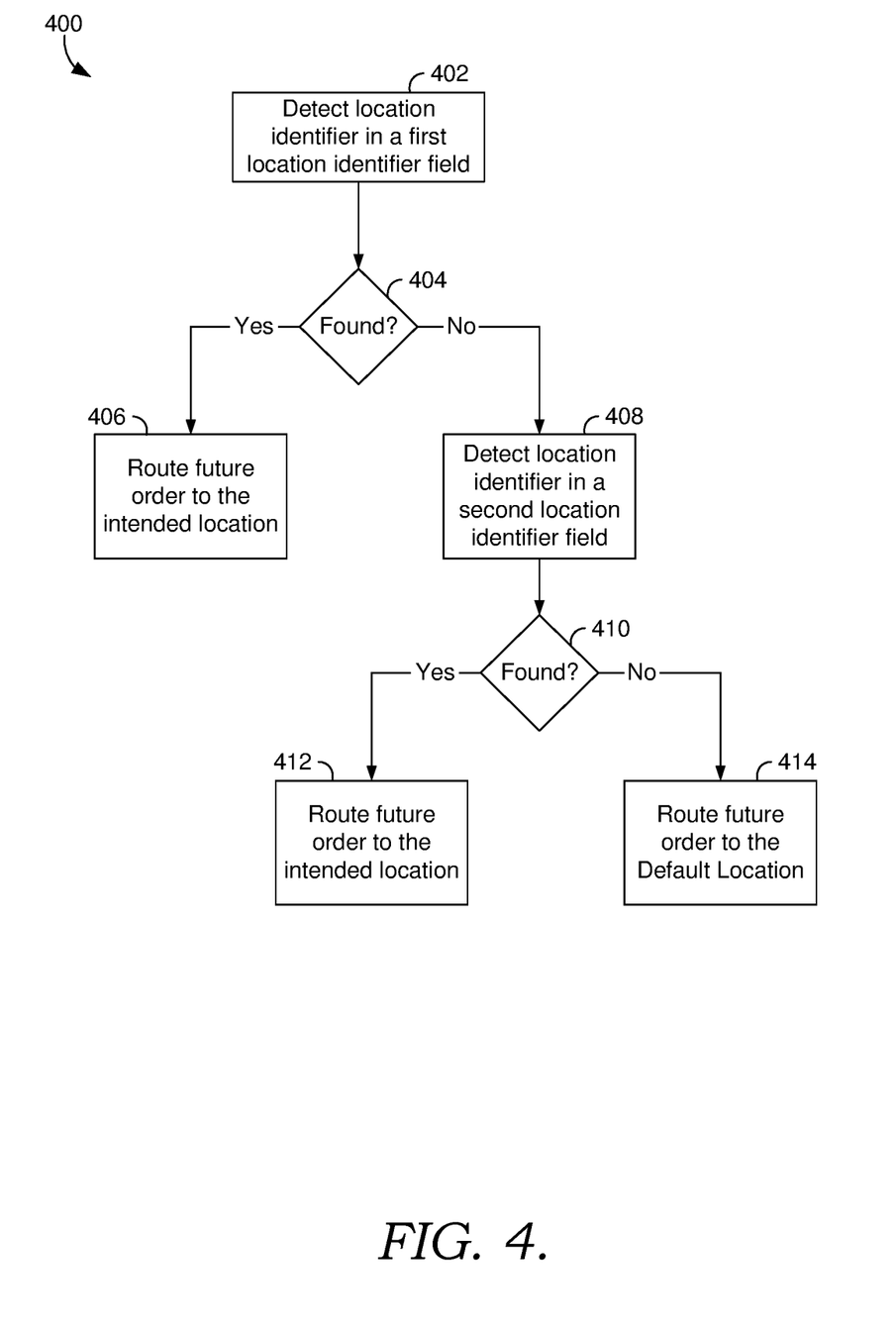
FIG. 4 is a flow diagram of an example algorithm for detecting location identifiers in specific location identifier fields, in accordance with aspects herein.

As discussed above, in certain aspects, a medical provider or organization utilizing an electronic medical records system or associated application may specify different fields of a future radiology order application as the location identifier field, in order to allow for customization. FIG. 4 provides an example algorithm 400 for determining if a location identifier is detected in one of the location identifier fields of a future radiology order. As can be seen in FIG. 4, step 402 begins with detecting a location identifier in a first location identifier filed of the future radiology order. The first location identifier field can be a preferred field for entering location identifiers that is unique to the systems and methods disclosed herein, e.g., to provide maximum detection efficiency and/or for ease of supplementation of a future radiology ordering application already in place. As such, this first location identifier field is examined first for detection of the location identifier. At step 404 it is determined if the location identifier is present at this first location identifier field. If the location identifier is detected in this first location identifier field, then at step 406 the future radiology order is routed to the intended radiology facility and/or radiologist, as discussed above. If at step 404 it is determined that the first location identifier field of the future radiology order does not include a location identifier, then at step 408, a second location identifier field is examined for the presence of the location identifier. In aspects, the second location identifier field can be an alternate field that can be used to supplement a future radiology ordering application, e.g., a field that is already in use in such an application but maybe for a different purpose than the systems and methods described herein. In such aspects, at the step 410, if it is determined that the location identifier is detected or is present in the second location identifier field, then at step 412, the future radiology order is routed to the intended radiology facility and/or radiologist, as discussed above. However, if at the step 410 it is determined that the second location identifier field also does not include a location identifier then the future radiology order, at step 414, is routed to a default facility or location. As discussed above, this default location may be where, in conventional systems, future radiology orders are received, which may not be the radiology facility intended to perform the ordered procedure.

Figure 5:
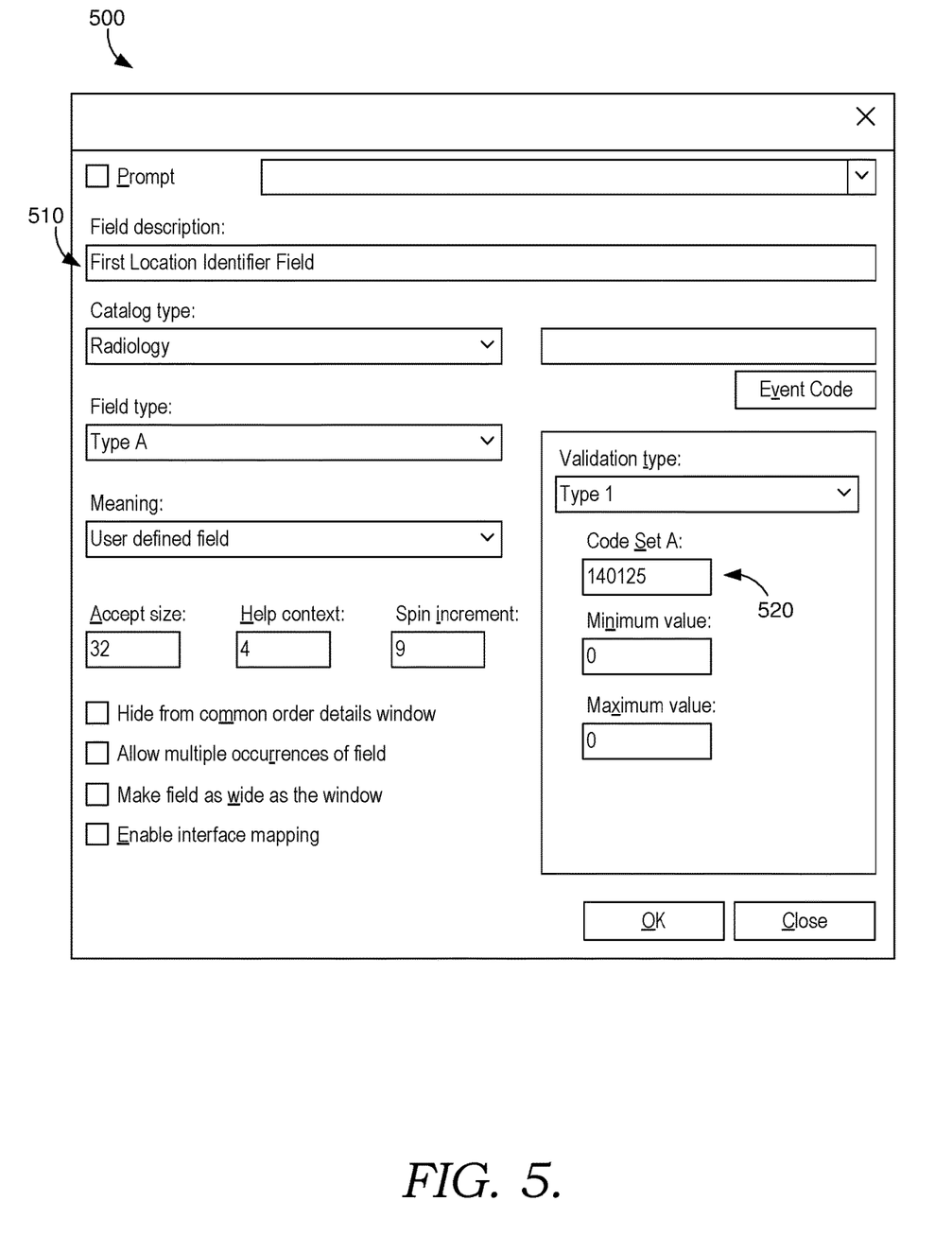
FIG. 5 is an example graphical user interface for designating a specific location identifier field for an application for creating future radiology orders, in accordance with aspects herein.
Figure 6:
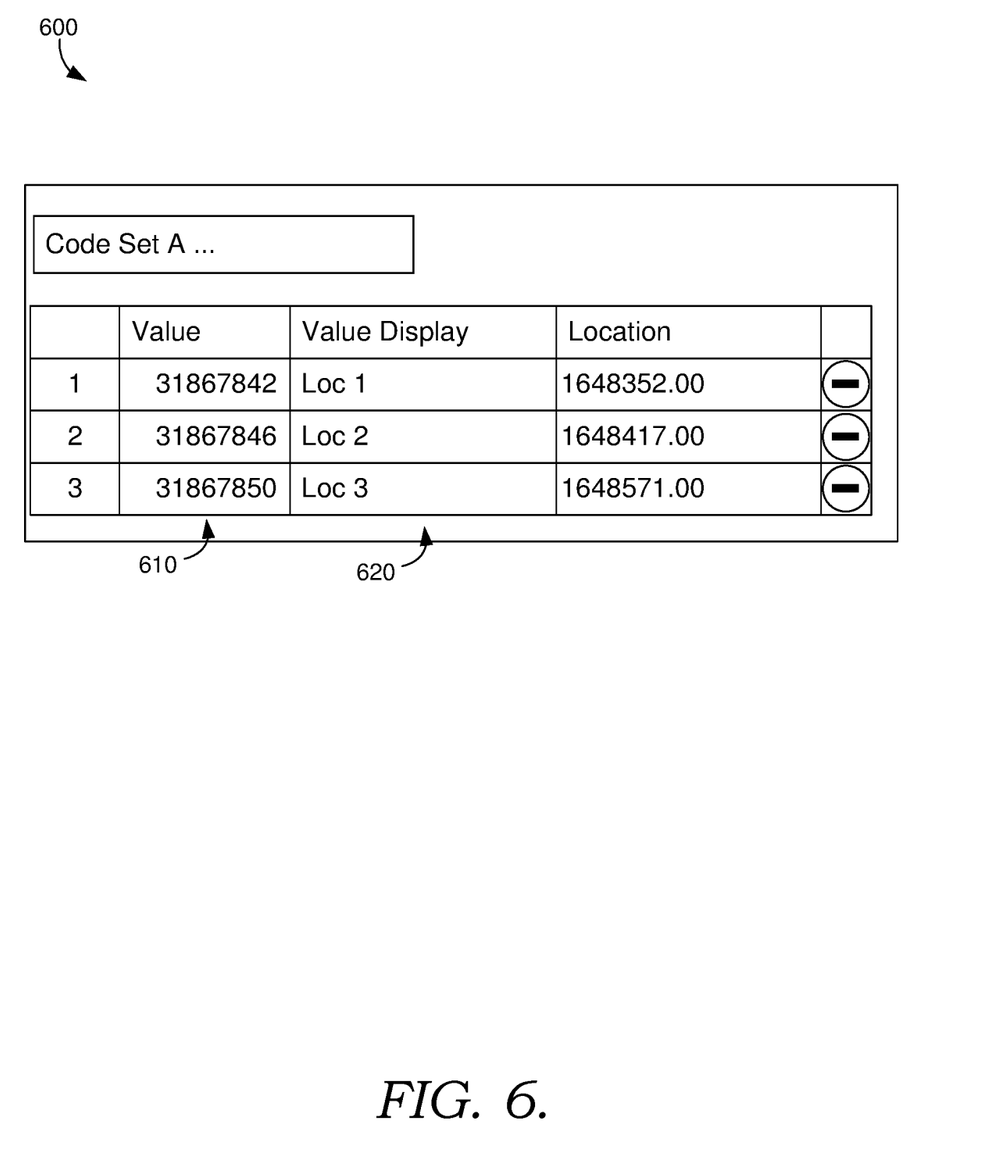
FIG. 6 is a graphical depiction of a code set and associated location descriptions, in accordance with aspects herein.

FIG. 5 depicts an example graphical user interface 500 that may be utilized to provide location identifiers in a specific field for an application for creating future radiology orders. As discussed above, in aspects, an end-user, e.g., a medical provider or organization, can customize how a location identifier is utilized in a current radiology ordering application. For instance, in aspects, an end-user may desire to add a new field, e.g., a location identifier field, to its radiology ordering application. In such aspects, the end-user can utilize self-created codes specific to their facilities. As can be seen in FIG. 5, the text input area 510 allows for adding a specific location identifier field and associated description in an application for generating future radiology orders. Further, at text input area 520, a specific code set can be referenced, which can include the specific end-user created codes. In such an aspect, the user interface 500 of FIG. 5, allows for a user to designate a specific location identifier field and reference a code set for use in the systems and methods disclosed herein. FIG. 6 is a display 600 depicting a table showing an association between the desired code set values for the location identifier field and a description of each code set value. As can be seen in FIG. 6, specific code set values 610 can be associated with specific descriptions of locations 620, e.g., radiology facilities. In aspects, an end-user can provide any desired description for the locations that can be displayed in the radiology ordering application.

Figure 7:
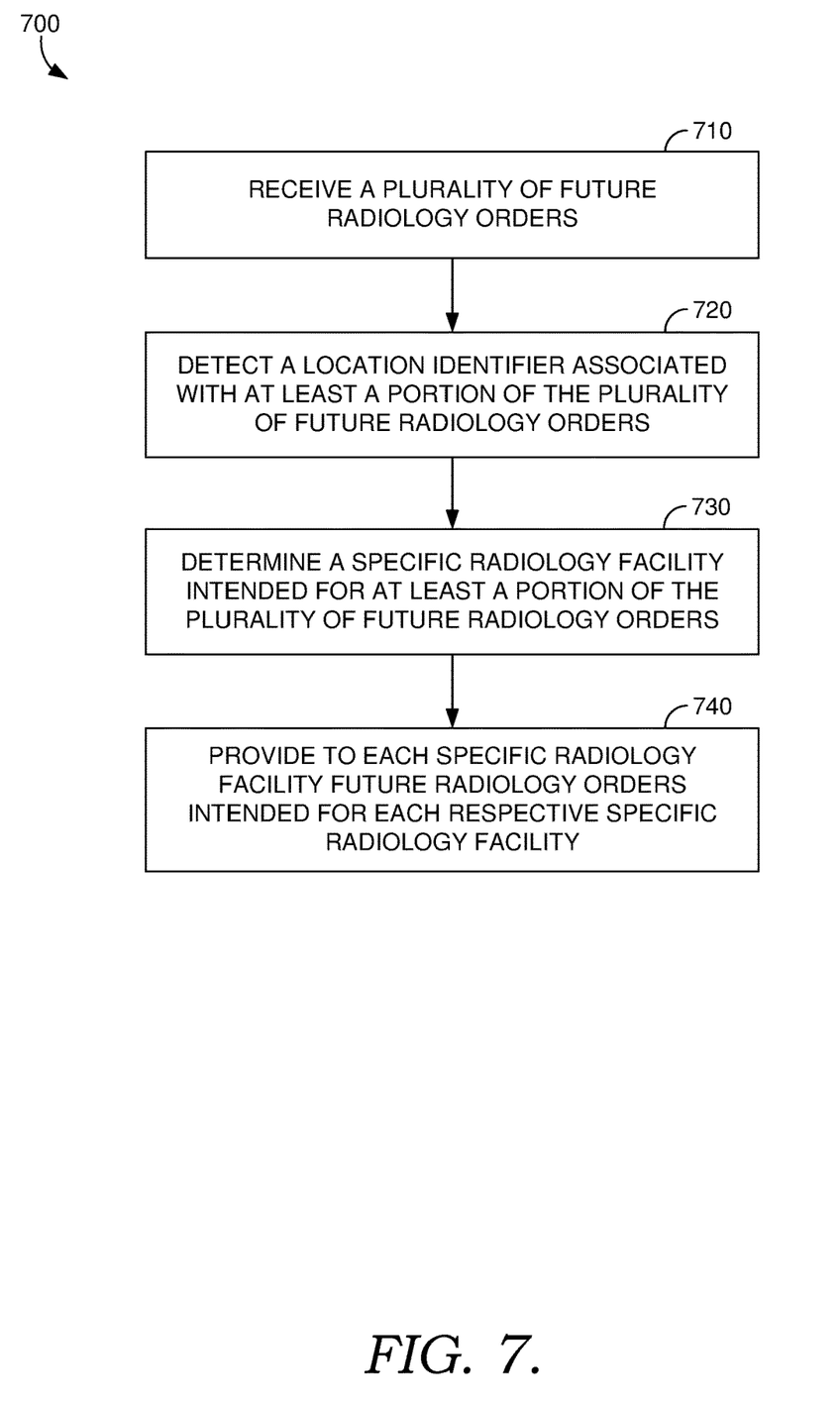
FIG. 7 illustrates a method for managing future radiology orders, in accordance with aspects herein.

FIG. 7 is a flow diagram of an example method for managing future radiology orders. In step 710 of the method 700, a plurality of future radiology orders is received. In various aspects, the first receiver 212 of the manager 210 of the system 200 can be utilized to receive the plurality of future radiology orders. In certain aspects, the plurality of future radiology orders can be obtained and/or received from a database, e.g., the database 230 of the system 200 described above with reference to FIG. 2.

In certain aspects, the plurality of radiology orders can include at least 20 future radiology orders, at least 50 future radiology orders, or at least 100 future radiology orders. In aspects, all or part of the plurality of future radiology orders can be associated with an electronic medical record. In aspects, the plurality of future radiology orders can include future radiology orders for a plurality of radiology facilities. In aspects, the plurality of future radiology orders can include future radiology orders for at least 10, at least 50, or at least 100 different radiology facilities or radiologists. In various aspects, the plurality of future radiology orders can include radiology orders that originated from a facility that is different from the radiology facility that is intended to be utilized for performing the radiology procedure or examination. In various aspects, the originating facility, e.g., where the future radiology order originated, and/or the intended radiology facility may be associated with a multi-facility medical provider or organization.

At step 720, the method 700 includes detecting a location identifier associated with at least a portion of the plurality of future radiology orders. In such aspects, the detector 214 of the manager 210 of the system 200 of FIG. 2 can be utilized for this step. In the same or alternative aspects, detecting a location identifier in one or more future radiology orders can include determining if a location identifier is provided in one or more location identifier fields of the future radiology order, as discussed above.

At step 730, the method 700 includes determining a specific radiology facility that is intended for at least a portion of the plurality of future radiology orders. In such aspects, determining a specific radiology facility that is intended for at least a portion of the plurality of future radiology orders can be based on the detection of a location identifier, such as that detected in step 720. In aspects, as discussed above, determining an intended radiology facility can include reading a location identifier in the future radiology order and associating the location identifier with a specific radiology facility, e.g., using a location identifier code set and associated location description information, as depicted in the example of FIG. 6. In various aspects, the determiner 216 of the manager 210 of the system 200 of FIG. 2 can be utilized to determine a specific radiology facility that is intended for at least a portion of the plurality of future radiology orders.

At step 740, the method 700 includes providing to each specific radiology facility, the future radiology orders for that intended radiology facility. In various aspects, the first provider 218 of the manager 210 of the system 200 of FIG.

2 can be utilized to provide to each specific radiology facility, the future radiology orders for that intended radiology facility. As discussed above, in aspects, the future radiology orders can be provided to the intended radiology facility and/or a radiologist by providing the future radiology orders to a device, server, or database associated with the intended radiology facility and/or intended radiologist.

As discussed above, once the future radiology orders are provided to the intended radiology facility and/or intended radiologist, the future radiology order can be vetted, so the future radiology orders can be confirmed, canceled, replaced, and/or scheduled.

Figure 8:
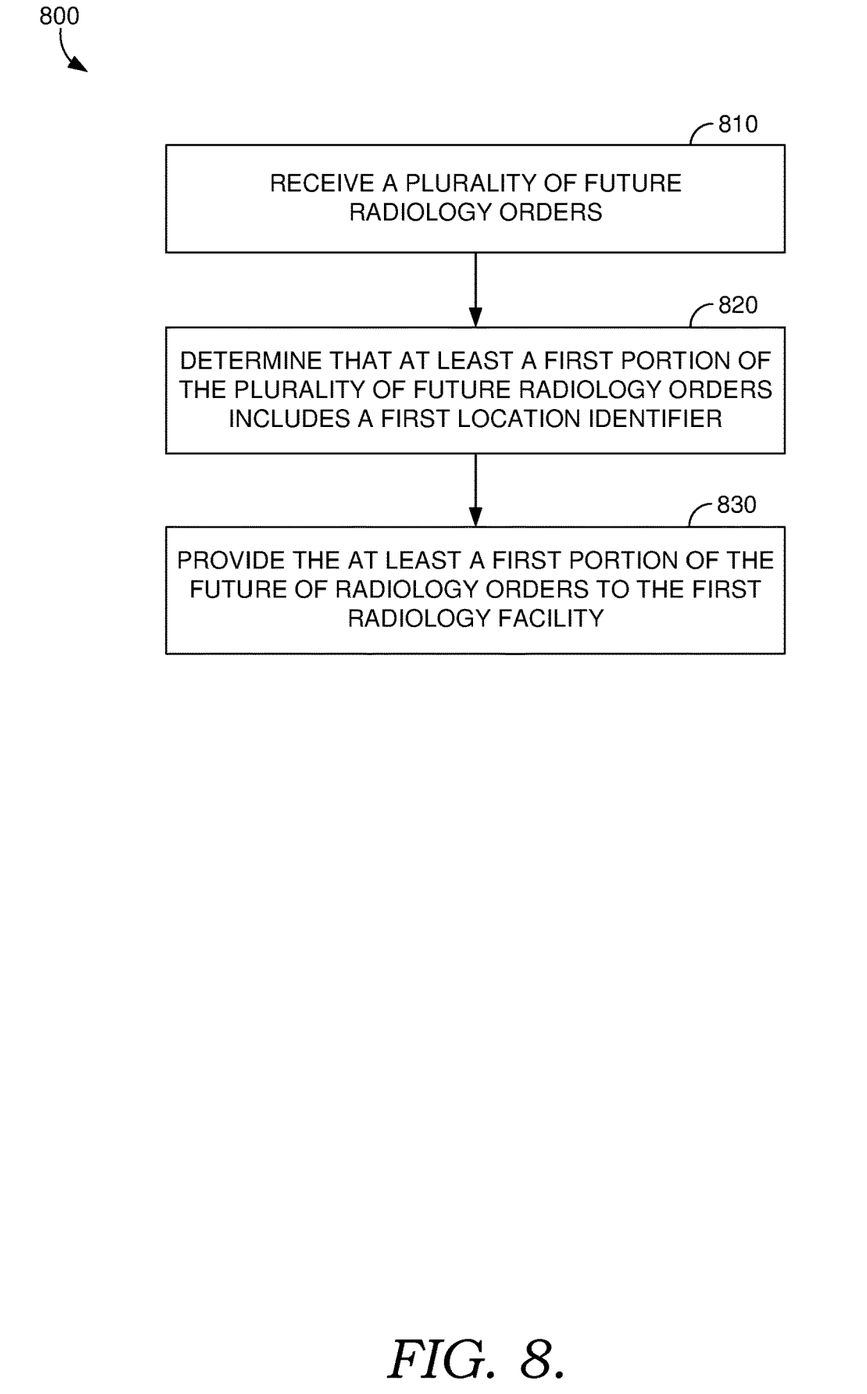
FIG. 8 illustrates another method for managing future radiology orders, in accordance with aspects herein.

FIG. 8 is a flow diagram of an example method for managing future radiology orders. In step 810 of the method 800, a plurality of future radiology orders is received. In various aspects, the first receiver 212 of the manager 210 of the system 200 can be utilized to receive the plurality of future radiology orders. In certain aspects, the plurality of future radiology orders can be obtained and/or received from a database, e.g., the database 230 of the system 200 described above with reference to FIG. 2.

As discussed above, in certain aspects, the plurality of radiology orders can include at least 20 future radiology orders, at least 50 future radiology orders, or at least 100 future radiology orders. In aspects, all or part of the plurality of future radiology orders can be associated with an electronic medical record. In aspects, the plurality of future radiology orders can include future radiology orders for a plurality of radiology facilities. In aspects, the plurality of future radiology orders can include future radiology orders for at least 10, at least 50, or at least 100 different radiology facilities or radiologists. In various aspects, the plurality of future radiology orders can include radiology orders that originated from a facility that is different from the radiology facility that is intended to be utilized for performing the radiology procedure or examination. In various aspects, the originating facility, e.g., where the future radiology order originated, and/or the intended radiology facility may be associated with a multi-facility medical provider or organization.

At step 820, the method 800 includes determining that at least a first portion of the plurality of future radiology orders includes a first location identifier. In aspects, as discussed above, determining that a future radiology order includes a location identifier can include reading or detecting a location identifier in a future radiology order, e.g., by determining if a location identifier is provided in one or more location identifier fields of the future radiology order. In various aspects, the determiner 216 of the manager 210 of the system 200 of FIG. 2 can be utilized to determine that at least a first portion of the plurality of future radiology orders includes a first location identifier.

At step 830, the method 800 can include providing at least a first portion of the future radiology orders to the first radiology facility. In aspects, the first provider 216 of the manager 210 of the system 200 of FIG. 2 can be utilized to provide at least a first portion of the future radiology orders to the first radiology facility. In various aspects as described above, the future radiology orders can be provided to the first radiology facility and/or a radiologist by providing the future radiology orders to a device, server, or database associated with the first radiology facility and/or intended radiologist. In aspects, once the future radiology orders are provided to the first radiology facility and/or intended radiologist, the future radiology order can be vetted, so the future radiology orders can be confirmed, canceled, replaced, and/or scheduled.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A computerized system comprising:
one or more processors; and
non-transitory computer storage media storing computer-useable instructions that, when used by the one or more processors, cause the one or more processors to:
receive, by a first computer, a plurality of future radiology orders via a network from at least one database, wherein the plurality of future radiology orders comprises radiology orders for a plurality of radiology facilities;
for a received radiology order from the plurality of future radiology orders, detect a location identifier associated with the received radiology order, wherein the location identifier corresponds to an intended radiological facility for the received radiology order;
based on detecting the location identifier, access a lookup table that converts the location identifier to a communication address associated with the intended radiological facility; and
automatically, by the first computer, route and transmit the received radiology order of the future radiology orders, via network communications that are configured based on at least the communication address, to a remote computer associated with the intended radiology facility that corresponds to the location identifier.

2. The computerized system of claim 1, wherein the instructions for detecting the location identifier are configured to identify a location identifier field associated with the received radiology order, and read the location identifier from the location identifier field.

3. The computerized system of claim 1, wherein the system is further configured to detect the location identifier, access the lookup table, and automatically route and transmit the received order for multiple orders from the plurality of future radiology orders.

4. The computerized system of claim 1, wherein one or more of the plurality of future radiology orders are provided from a facility that is different from the plurality of radiology facilities.

5. The computerized system of claim 1, wherein the computer-useable instructions further cause the one or more processors to: determine that at least one order of the plurality of future radiology orders does not include a location identifier; and
provide the at least one order of the plurality of future radiology orders to a default radiology facility, wherein the default radiology facility is not an intended radiology facility for the at least one order of the plurality of future radiology orders.

6. The computerized system of claim 1, wherein the plurality of future radiology orders comprise orders for a radiology procedure or examination that is intended to be conducted at least one week after the future radiology order was provided.

7. The computerized system of claim 1, wherein the computer-useable instructions further cause the one or more processors to:

receive, from a first radiology facility, a query for future radiology orders that are intended to be performed at the first radiology facility over a defined time period, wherein the query includes a location identifier for the first radiology facility; and provide to the first radiology facility future radiology orders for the first radiology facility over the defined time period.

8. The computerized system of claim 7, wherein the defined time period includes a period of at least two weeks from a time that the query was received.

9. The computerized system of claim 8, wherein the computer-useable instructions further cause the one or more processors to: receive, from the first radiology facility, a replacement radiology order for at least one of the provided future radiology orders for the first radiology facility.

10. The computerized system of claim 1, wherein the computer-useable instructions further cause the one or more processors to: receive a ranking of received future radiology orders for a specific radiology facility.

11. A non-transitory computer storage media storing computer-executable useable instructions that, when executed by the one or more processors, cause the one or more processors to:

receive, by a first computer, a plurality of future radiology orders via a network from at least one database, wherein the plurality of future radiology orders comprises radiology orders for a plurality of radiology facilities;

determine, by the first computer, that at least a first portion of the plurality of future radiology orders includes a first location identifier, wherein the first location identifier is associated with a first radiology facility;

based on the first location identifier, access a lookup table that converts the first location identifier to a communication address associated with the first radiological facility; and automatically, by the first computer, route and transmit at least the first portion of the future of radiology orders, via network communications that are configured based on at least the communication address, to a remote computer associated with the first radiology facility based on the first location identifier.

12. The non-transitory computer storage media of claim 11, wherein one or more of the plurality of future radiology orders are provided from a facility that is different from the plurality of radiology facilities.

13. The non-transitory computer storage media of claim 11, wherein the plurality of future radiology orders comprise orders for individuals not present at one of the plurality of radiology facilities at the time the respective orders were created.

14. The non-transitory computer storage media of claim 11, wherein the plurality of radiology facilities comprises at least ten radiology facilities at distinct locations.

15. The non-transitory computer storage media of claim 11, wherein the computer-useable instructions further cause the one or more processors to: receive, from the first radiology facility, a replacement order for one of the at least a first portion of future radiology orders.

16. The non-transitory computer storage media of claim 11, wherein the computer-useable instructions further cause the one or more processors to: receive, from the first radiology facility, a confirmation, from a medical professional, for one order of the first portion of the future radiology orders.

17. The non-transitory computer storage media of claim 11, wherein the computer-useable instructions further cause the one or more processors to:

determine that at least a second portion of the plurality of future radiology orders includes a second location identifier, the second location identifier associated with a second radiology facility;

based on the second location identifier, access the lookup table that converts the second location identifier to a second communication address associated with the second radiological facility; and automatically, by the first computer, route and transmit the second portion of the future of radiology orders, via network communications that are configured based on at least the second communication address, to a second remote computer associated with the second radiology facility.

18. The non-transitory computer storage media of claim 11, wherein the first location identifier is provided in the at least the first portion of the plurality of future radiology orders at the time of order creation.

19. A computerized method comprising:

retrieving, by a first computer via a communication network, a plurality of radiology orders as data records from a database;

detecting, by the first computer from the data records, whether a location identifier is associated with at least a portion of the plurality of radiology orders, wherein the location identifier of a given radiology order designates an intended radiology facility for the given radiology order from the plurality of radiology facilities;

based on identifying the location identifier, accessing a lookup table that converts location identifiers to an assigned communication address associated with a destination radiological facility; and automatically, by the first computer, route and transmit each radiology order via network communications that are configured based at least on the assigned communication address, to a remote computer associated with the destination radiology facility based on the location identifier associated with each radiology order.

20. The computerized method of claim 19, wherein the method further comprises receiving, from a first radiology facility, a confirmation from a medical professional for one of the at least a portion of the radiology orders, a replacement order for one of the at least a portion of the radiology orders, or a combination thereof.

* * * * *